United States Patent [19]

Ohba et al.

[11] 4,220,639
[45] Sep. 2, 1980

[54] ANTIBIOTICS SF-2050 AND SF-2050B SUBSTANCES AND PRODUCTION AND USE THEREOF

[75] Inventors: Kazunori Ohba; Chuhei Nojiri; Yasuaki Ogawa; Jiro Itoh, all of Yokohama; Kunikazu Totsugawa, Tokyo; Norio Ezaki, Yokohama; Takashi Shomura, Yokohama; Tomizo Niwa, Yokohama; Shigeharu Inouye, Yokohama; Yujiro Yamada, Yokahama, all of Japan

[73] Assignee: Meiji Seika Kaisha, Ltd., Tokyo, Japan

[21] Appl. No.: 6,873

[22] Filed: Jan. 26, 1979

[30] Foreign Application Priority Data

Feb. 14, 1978 [JP] Japan ................................ 53-15026
Mar. 14, 1978 [JP] Japan ................................ 53-28324

[51] Int. Cl.² .................... C12D 9/14; A61K 35/00
[52] U.S. Cl. .................................. 424/117; 435/130; 435/169; 435/886
[58] Field of Search ..................... 195/80 R; 424/117; 435/130, 169

[56] References Cited

U.S. PATENT DOCUMENTS

3,928,569  12/1975  Umezawa et al. .................... 424/117

Primary Examiner—Lionel M. Shapiro
Attorney, Agent, or Firm—Larson, Taylor and Hinds

[57] ABSTRACT

New antibiotics, SF-2050 substance and SF-2050B substance are produced by cultivating a microorganism Streptomyces sp. SF-2050 now deposited under FERM-P 4358 and under ATCC. 31450 in a liquid culture medium under aerobic conditions, and these antibiotics may be isolated from the fermentation broth and useful as an antibacterial agent. These antibiotics have an activity inhibitory to $\beta$-lactamase.

8 Claims, 8 Drawing Figures

ANTIBIOTICS SF-2050 AND SF-2050B SUBSTANCES AND PRODUCTION AND USE THEREOF

SUMMARY OF THE INVENTION

This invention relates to new and useful two antibiotics designated as SF-2050 substance and SF-2050B substance. This invention also relates to a process for the production of these new antibiotics by cultivating a strain of the genus Streptomyces. This invention further relates to an antibacterial composition comprising at least one of the SF-2050 substance and SF-2050B substances as the active ingredient.

BACKGROUND OF THE INVENTION

A number of useful antibiotics are produced in and isolated from the culture broth of various strains of the genus Streptomyces. In an attempt to find out new and useful antibiotics active against gram-negative and gram-positive bacteria as well as various bacteria strains resistant to the known antibiotics, we have made research on the fermentation broth of a new microorganism designated as Streptomyces sp. SF-2050. As a result, we have now found that new and useful two antibiotics are produced by incubating Streptomyces sp. SF-2050 in a culture medium comprising assimilable nutrients. We have succeeded to isolate these two active substances from the culture broth and have designated them as SF-2050 substance and SF-2050B substance, respectively. We have now determined the chemical and physical properties of these new antibiotics. Furthermore, these new antibiotics have found to have an activity inhibitory to β-lactamase.

An object of this invention is to provide new antibiotics which are useful as antibacterial agent and as an inhibitor to β-lactamase. A further object of this invention is to provide a process of producing these useful antibiotics. Another objects will be clear from the following descriptions.

DETAILED DESCRIPTION OF THE INVENTION

According to a first aspect of this invention, therefore, there is provided a process for the production of new antibiotics, SF-2050 substance and/or SF-2050B substance, which comprises cultivating a strain of the genus Streptomyces capable of producing SF-2050 substance and SF-2050B substance in an aqueous liquid culture medium containing assimilable carbon and nitrogen sources under aerobic conditions for a period of time sufficient to produce and accumulate at least one of SF-2050 substance and SF-2050B substance in the culture, and then recovering at least one of the SF-2050 substance and SF-2050B substance from the culture.

In carrying out the process of this invention, any strain of the genus Streptomyces may be used as far as it substantially produces both of SF-2050 substance and SF-2050B substance in the culture thereof. A specific example of the strain which may be used suitably in the present process is the strain SF-2050 which was isolated from a soil sample collected in Ibaragi-prefecture, Japan and which has now been designated as Streptomyces sp. SF-2050. This strain SF-2050 has been deposited in a Japanese public depository "Fermentation Research Institute", Chiba-city, Japan, under deposit number FERM-P 4358 and also in the American Type Culture Collection, Washington, D.C., U.S.A., under deposit number ATCC. 31450 as of November 9, 1978.

The strain SF-2050 has the following microbiological characteristics:

I. Morphological observation

Substrate mycelia are abundantly grown on various culture media while the formation of aerial mycelia is generally poor. On inorganic salts-starch-agar, tyrosine-agar or sucrose-nitrate-agar media where aerial mycelia develop relatively well, the aerial mycelia produce monopodially branches, no whorl-branching being observed. The tips of aerial mycelia appear to be straight. No special structure such as sclerotium is observed.

Electron-microscopic observation shows that the surface structure of the spores is smooth. The spores are of elliptical shape to short cylindrical shape and have a size of 0.5–0.8 microns by 0.8–1.4 microns.

II. Cultural characteristics on different culture media

The cultural characteristics of the strain SF-2050 are shown in Table 1 below. In the following table, the description of colors given in a bracket [ ] are based on the standard of Color Harmony Mannual of Container Corporation of America. The incubation temperature was 28° C. and the observation was made after incubation for 14–21 days.

Table 1

| Culture medium | Growth, color of reverse side | Aerial mycelium | Soluble pigment |
|---|---|---|---|
| Sucrose-nitrate agar | Ordinary growth, colorless to faintly pearl | Faintly shell-pink [3 ca] | None |
| Glucose-asparagine agar | Thin growth, yellow to yellowish brown | Poor, white to faintly yellow | None |
| Glycerol-asparagine agar | Ordinary growth, faintly pearl | Poor, white to faintly pearl [2 ba] | None |
| Inorganic salts-starch agar | Good growth, faintly yellow to yellowish brown | Shell-pink to pale melon-yellow [3 ca to 3 ea] | None |
| Oatmeal agar | Ordinary growth, yellow to lemon yellow | Very poor, white to pale yellow | None |
| Yeast extract-malt extract agar | Good growth, pale brown | Poor, shell-pink [3 ca] | None |
| Tyrosine agar | Good growth, pale brown | Faintly shell-pink to pale yellow [3 ca to 1½ db] | None |
| Nutrient agar | Ordinary growth, pale yellow | Poor, white | None |

III. Physiological properties
 (1) Growth temperature range: The strain SF-2050 grows in a temperature range of 20–33° C. on starch-agar medium. The optimum growth temperature is in a range of 25–30° C.
 (2) Liquefaction of gelatine: Positive (at 20° C., 14 days incubation).
 (3) Hydrolysis of starch: Positive (at 20° C.).
 (4) Coagulation of skimmed milk: Negative (at 28° C.).
 (5) Peptonization of skimmed milk: Positive (at 28° C.).

(6) Chromogenicity: Negative.

IV. Utilization of carbon sources (estimated in Pridham-Gottlieb's agar medium incubated at 28° C.)
  (1) Utilizable: D-glucose, rhamnose.
  (2) Doubtful: D-xylose, L-arabinose.
  (3) Not utilizable: D-fructose, D-mannitol, I-inositol, sucrose, raffinose.

V. Diaminopimelic acid (DAP) in the hydrolysate of the whole cell: LL-form.

The above-mentioned characteristics of the strain SF-2050 may be summarised as follows: The strain SF-2050 belongs to the genus Streptomyces, and the aerial mycelia are straight at the tip thereof and the surface structure of the spores is smooth. The color of the aerial mycelia is initially white to pale yellow and becomes shell-pink occasionally with yellow tinge as the strain matures. The strain SF-2050 belongs to the Red or Yellow series according to Tresner and Backus (H. D. TRESNER and F. J. BACKUS: Appl. Microbiol. 11, 335 (1963)). The reverse side of the growth is yellow to pale brown colored, and no soluble pigment is produced on any culture medium.

The strain SF-2050 has properties which are liable to vary as may be usually observed with other species of Streptomyces. Thus, for example, the strain SF-2050 may produce variants or mutants when treated with various mutagens such as ultraviolet rays, X-rays, high-frequency electromagnetic waves, radioactive rays and chemicals. Therefore, any strain of the genus Streptomyces, including any natural or artificial variant and mutant of the aforesaid strain SF-2050, may be used in the process of this invention, so long as it has the ability to produce the SF-2050 substance or the SF-2050B substance or both of them.

In carrying out the process of this invention, the strain for present use may be cultivated in a manner known per se in a culture medium containing nutrient sources which are assimilable by ordinary microorganisms. For this purpose, use may be made of any known nutrients which have been generally employed for the cultivation of known strains of the genus Streptomyces. Examples of the nutrient sources include glucose, glycerine, starch, starch syrup, molasses and soybean oil as the carbon sources; and soybean meal, wheat embryo, dried yeast, peptone, meat extract, corn steep liquor, ammonium sulfate and sodium nitrate as the nitrogen sources. If required, inorganic salts such as calcium carbonate, sodium chloride, potassium chloride, cobalt chloride, phosphates and the like may be added. In addition, such organic and inorganic materials as to aid the growth of the strain used and to promote the production of the SF-2050 substance and SF-2050B substance may be incorporated in the culture medium. Addition of cobalt ion particularly promotes of the production of the desired antibiotics.

As the cultivation methods which can be employed in this invention, liquid cultivation, particularly under submerged aerobic conditions is most preferred as is generally used in the production of known antibiotics. In the present process, the cultivation is conducted under aerobic conditions, suitably at a temperature of 22° to 30° C. and most frequently at a temperature in the vicinity of 28° C. In this situation, the production of the SF-2050 and SF-2050B substances in the culture broth reaches a maximum at the end of 1 to 4 days of fermentation, either in shake-cultivation methods or in tank-cultivation methods.

For assay of the SF-2050 substance and SF-2050B substance according to this invention, the following procedure may be used: the assaying culture medium comprising 0.1% glucose, 0.5% tryptone, 0.25% yeast extract and 1.5% agar (pH 7.0). As the assaying microorganism is used Bacillus stearothermophilus. The assay may usually be conducted according to the conventional paper-disc method in such a manner that the diameter of the inhibition zone is determined after incubation at 55° C. for 16-18 hours.

The SF-2050 substance and SF-2050B substance according to this invention are both a compound of an acidic nature which contains a carboxylic group (—COOH) and a sulfonic group (—$SO_3H$) in the molecule thereof and which has physico-chemical properties as stated hereinafter, and hence by taking advantage of the physico-chemical properties of the SF-2050 and SF-2050B substances, they can be recovered from the culture broth of the SF-2050 strain and then purified. For instance, the SF-2050 substance and SF-2050B substance can be recovered from the fermentation broth of the strain SF-2050 and isolated by the following procedure: The fermentation broth containing the SF-2050 and SF-2050B substances is filtered to remove the solids, and the broth filtrate so obtained is treated with active carbon to make the desired antibiotics adsorbed by the active carbon which is then eluted with 50% aqueous acetone (a mixture of water and acetone at a ratio of 1:1 by volume). The eluate is collected in fractions, and the fractions containing the active substances are combined together and concentrated by evaporation of water and acetone under reduced pressure. The resulting concentrated solution is then distilled under reduced pressure to remove the acetone, and the residue is extracted with an organic solvent such as a halogenoalkane, eg. dichloromethane containing a quantity of a quaternary ammonium salt such as benzyldimethylcetyl ammonium chloride or tetra-n-butyl ammonium hydrogen sulfate dissolved therein. The extract so obtained is again extracted with water containing sodium iodide. The resulting aqueous solution containing the SF-2050 and SF-2050B substances is then freeze-dried to afford a crude powder comprising SF-2050 substance and SF-2050B substance. For the purification and isolation, this crude powder is subjected to a chromatographic method using an anion-exchanger such as DEAE-Sephadex A-25, QAE-Sephadex A-25, DEAE-cellulose or Dowex 1×2 to give the active fractions containing the SF-2050 substance and the different, active fractions containing the SF-2050B substance. DEAE-Sephadex A-25 is a product of Pharmacia Co., Sweden and consisting of diethylaminoethyl dextran. The purification may also be achieved by using a column of a gel-filtration agent such as "Bio-gel" (a product of Bio Rad Laboratory and consisting of polyacrylamides) or a synthetic adsorbent resin such as Amberlite XAD (a synthetic adsorbent resin consisting of a microporous copolymer of styrene and divinylbenzene, a product of Rohm & Haas Co., U.S.A.). The active fractions containing solely the SF-2050 substance or the active fractions containing solely the SF-2050B substance are concentrated to dryness under reduced pressure to yield a purified powder of the SF-2050 substance or the SF-2050B substance which gives a single spot on a thin layer chromatography on silica gel or cellulose as developed with various solvents as the eluent.

The SF-2050 substance and the SF-2050B substance of this invention are very unstable at an elevated temperature higher than ambient temperature and also under acidic conditions as shown hereinafter. For the recovery of the SF-2050 substance and SF-2050B substance from the fermentation broth, therefore, it is very important that care is taken to prevent the solutions from becoming acidic in the course of the recovery and purification steps, and that the treatments of the solutions are conducted rapidly at a low temperature.

As the SF-2050 substance and SF-2050B substance are very instable under the acidic conditions, it is practically difficult to isolate them in the form of the free acid. For this reason, it is preferred in practice that SF-2050 substance and SF-2050B substance are recovered as their alkali metal salt such as sodium salt, potassium salt or barium salt in the form of amorphous powder by freeze-drying a neutralized solution of SF-2050 substance or SF-2050B substance in water. The purity of the salt so obtained can sometime vary depending on the potency or the content of the antibiotics in the fermentation broth to be processed. The nature of the salt of the SF-2050 substance or SF-2050B substance is decided by the cation which is present in the solutions employed for the treatment of the SF-2050 substance and SF-2050B substance in the course of the recovery and purification thereof. For instance, the SF-2050 substance or SF-2050B substance is obtained as its di-sodium salt when aqueous solution of sodium chloride is employed as the eluent in the chromatographic process on DEAE-Sephadex A-25 for the purification of the desired antibiotics. In addition to the di-sodium salt, the SF-2050 substance or SF2050B substance may also be the other, pharmaceutically acceptable salts as an alkali metal salt such as di-potassium salt, an alkaline earth metal salt such as calcium salt, barium salt, ammonium salt or aluminum salt (the inorganic salt), or alternatively a salt with a substituted ammonium such as quaternary ammonium salt (the organic salt). These pharmaceutically acceptable salts may be prepared in the same manner as the aforesaid di-sodium salt. The di-sodium salt of SF-2050 substance or SF-2050B substance may be converted into another salt with a different cation by passing an aqueous solution of said di-sodium salt through a column of a cation-exchange resin such as Dowex 50W of which the hydrogen ions have been replaced by the desired cation.

The SF-2050 substance and SF-2050B substance obtained by the process of this invention are both new and useful antibiotics as stated hereinbefore and illustrated hereinafter.

Figure 2:
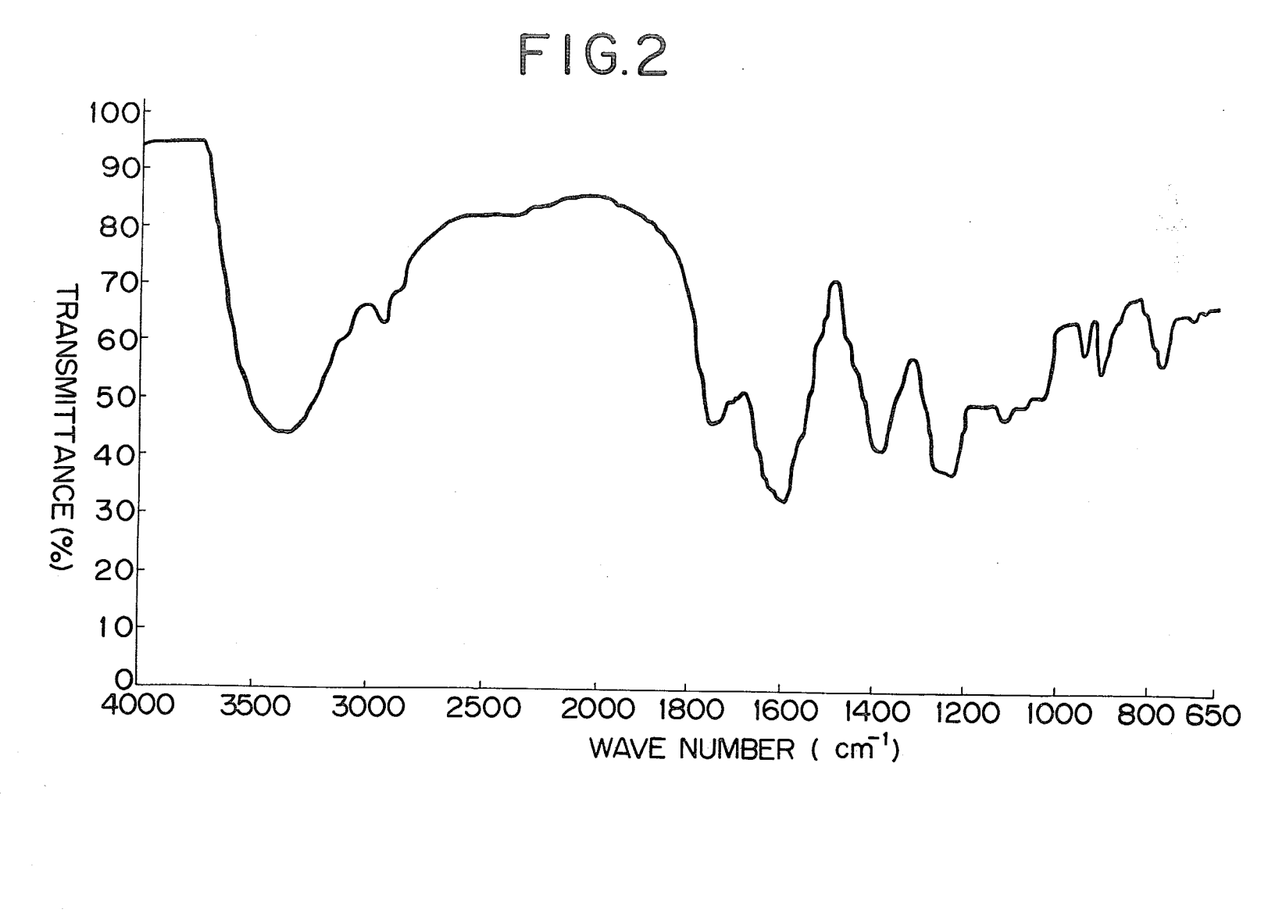
FIG. 2 shows a curve of the infrared absorption spectrum of a sample of the sodium salt of SF-2050 substance of this invention pelleted in potassium bromide.
Figure 3:
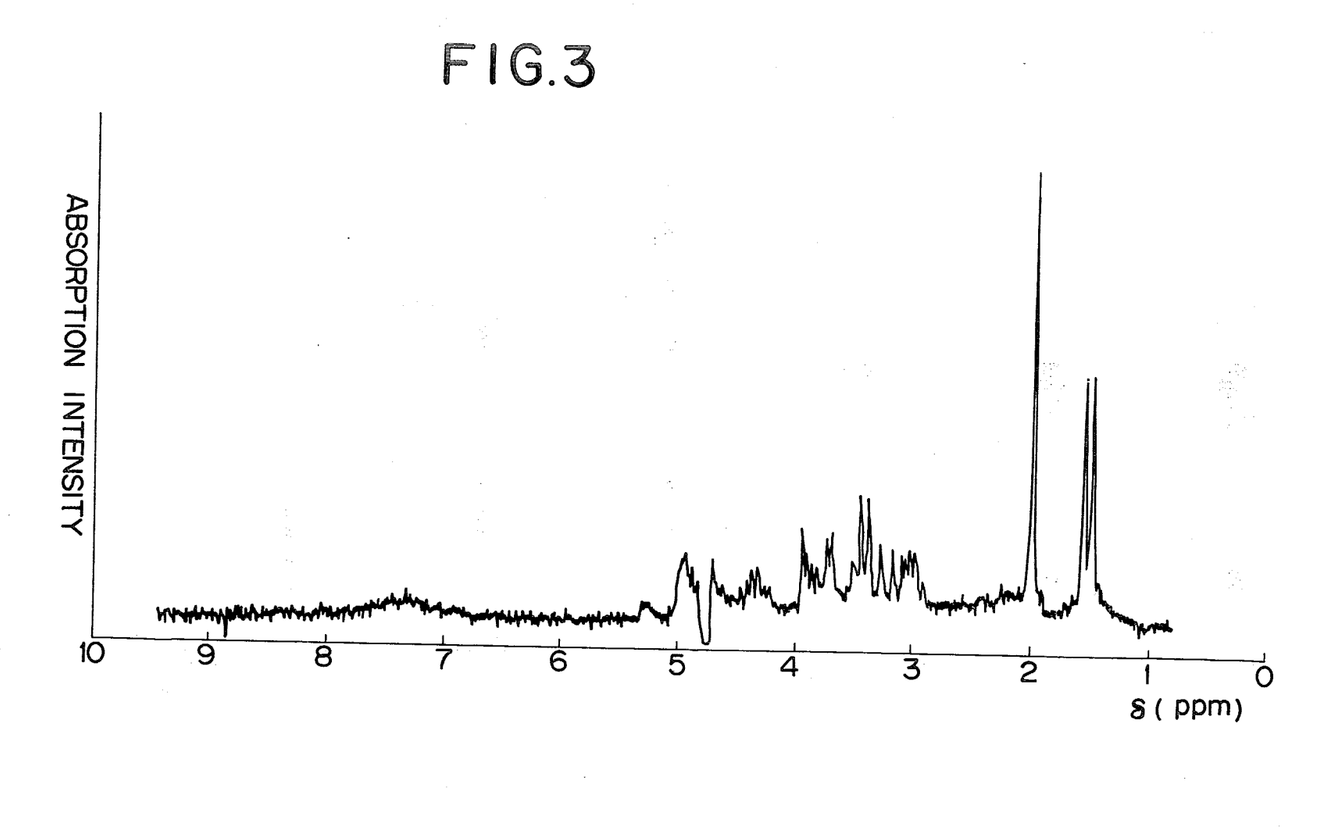
FIG. 3 shows a curve of the hydrogen nuclear magnetic resonance absorption spectrum of a sample of the sodium salt of SF-2050 substance determined in deutero-water at 100 MHz.
Figure 6:
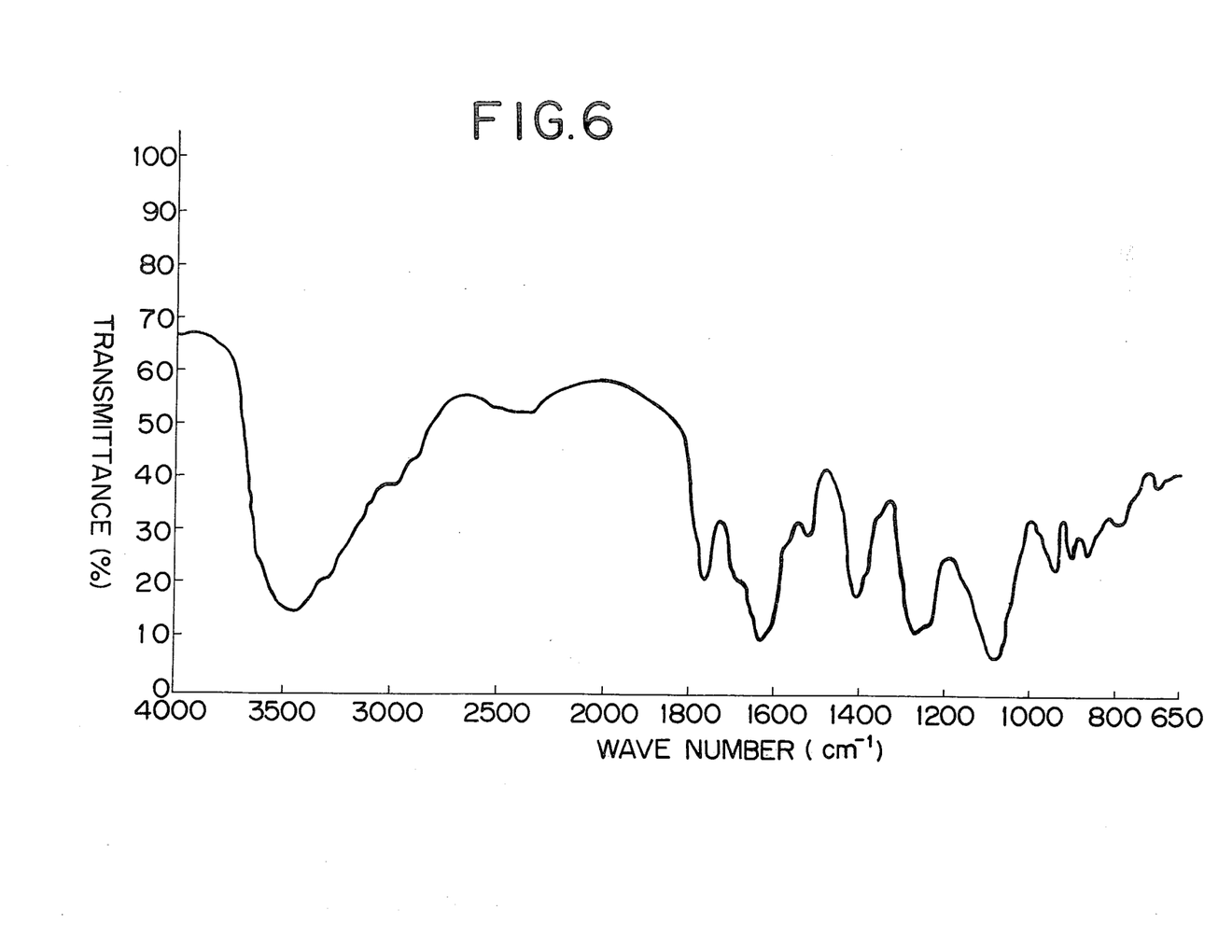
FIG. 6 shows a curve of the infrared absorption spectrum of a sample of the sodium salt of SF-2050B substance pelleted in potassium bromide.
Figure 7:
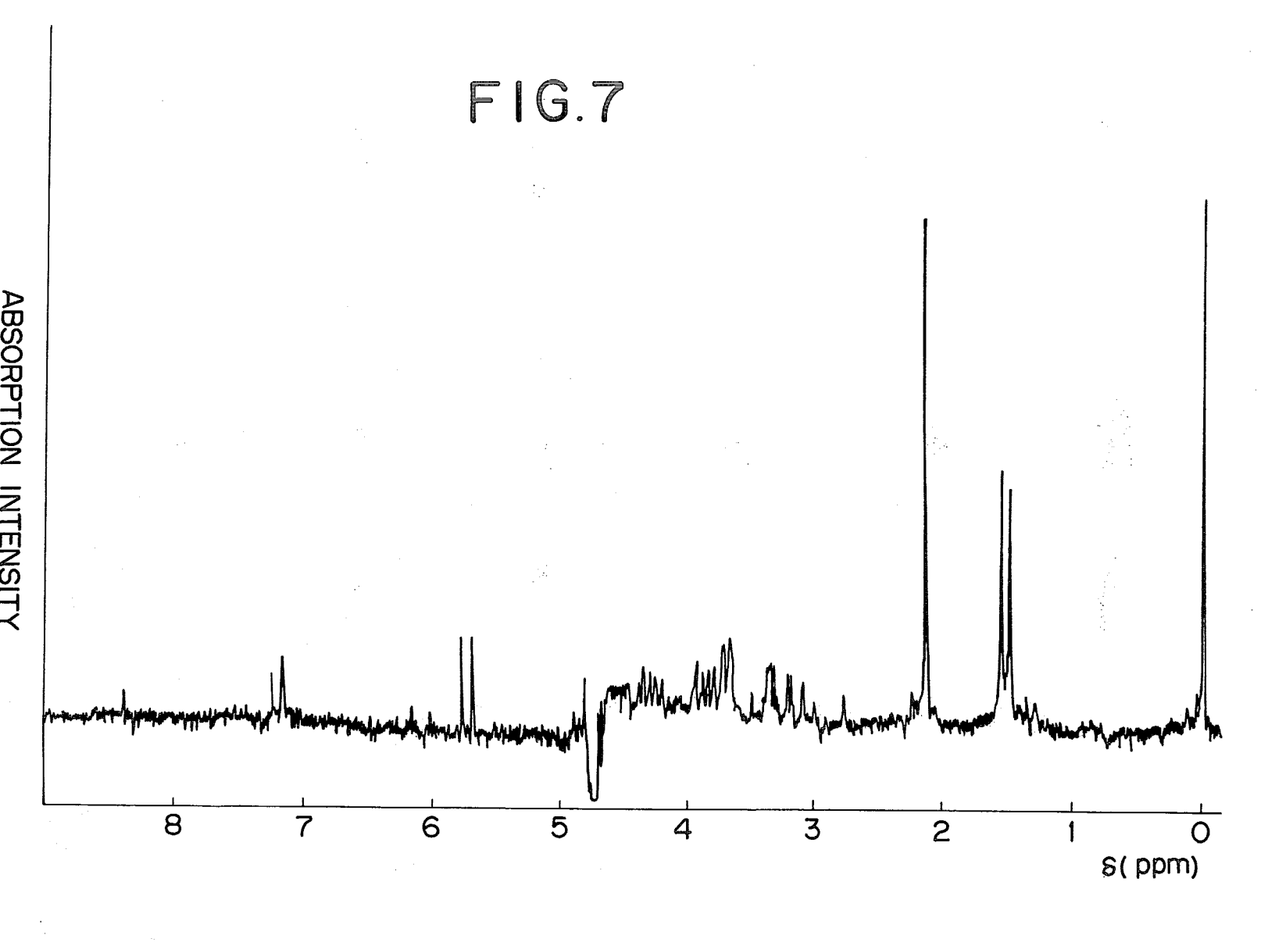
FIG. 7 shows a curve of the hydrogen nuclear magnetic resonance spectrum of a sample of the sodium salt of SF-2050B substance determined in deutero-water at 100 MHz.
Figure 8:
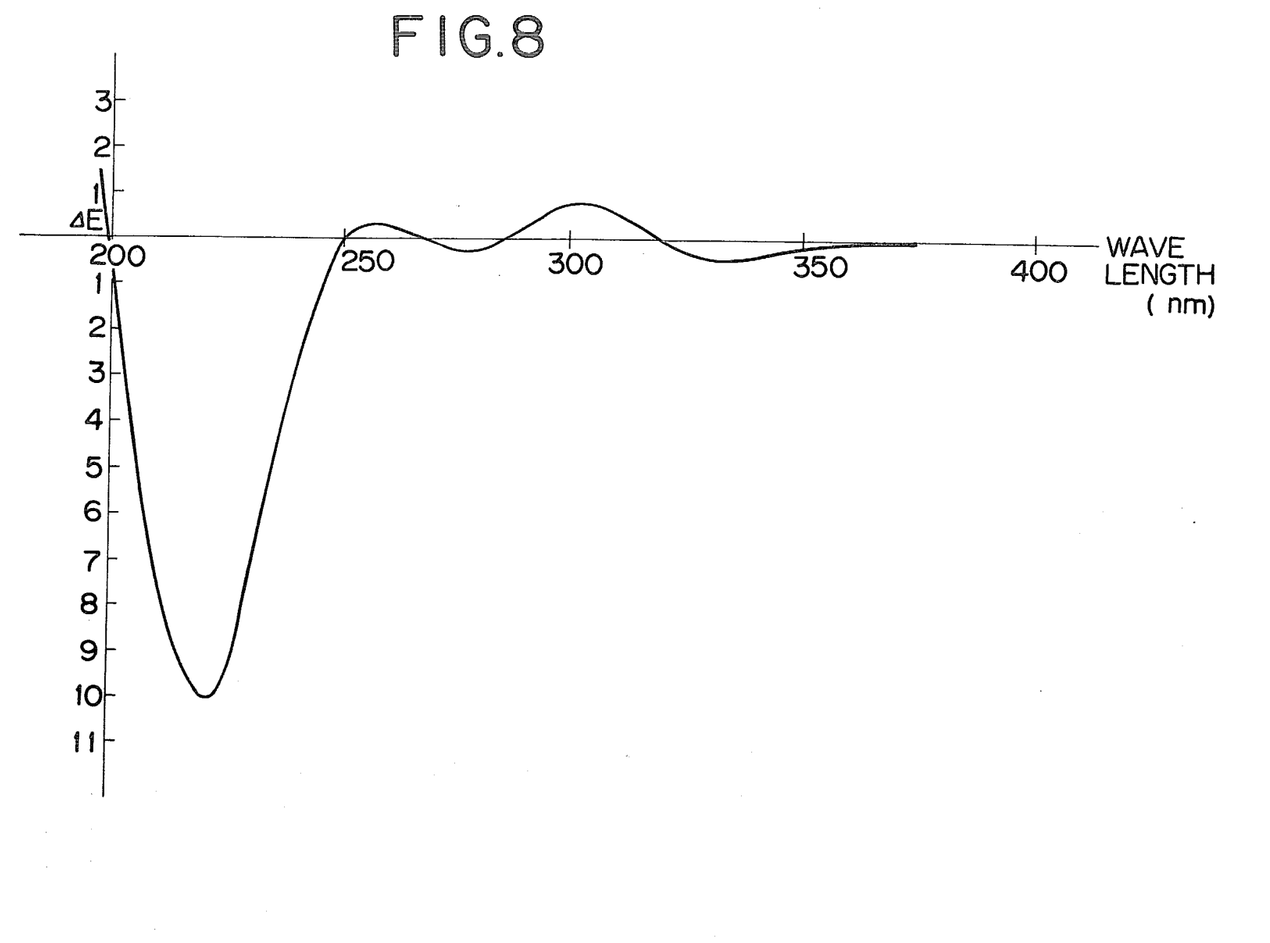
FIG. 8 shows a curve of the circular dichroism spectrum of a sample of the sodium salt of SF-2050B substance determined in 1/100 M buffered phosphate solution, pH 6.5.

According to a second aspect of this invention, therefore, there is provided a new substance selected from the SF-2050 substance, SF-2050B substance and pharmaceutically acceptable salts thereof;

the SF-2050 substance and SF-2050B substance being both a dibasic acid compound of which the sodium salt is in the form of a colorless powder having no definite melting point and shows negative reaction with ninhydrin but positive reaction with sodium iodide and of which the di-sodium salt is a colorless powder soluble in water, less soluble in methanol and sparingly soluble in ethyl acetate, chloroform and benzene;

the SF-2050 substance being further characterized by:

(a) being a dibasic acid which moves towards anode in a high-voltage filter paper electrophoresis at pH 6.7 and shows a mobility of 1.6 when the mobility of cephamycin A is assumed to be 1.0 in this electrophoresis;

and the di-sodium salt of SF-2050 substance being further characterized by:

(b) having a characteristic absorption peak at 295 nm in ultraviolet absorption spectrum in aqueous solution;

(c) having an infrared absorption spectrum pelleted in potassium bromide corresponding to that shown in FIG. 2 of the attached drawings (peaks at 3350, 2940, 1750, 1600, 1390, 1250, 1230, 1120, 940, 900 and 770 $cm^{-7}$);

(d) having a hydrogen nuclear magnetic resonance absorption spectrum in deutero-water corresponding to that shown in FIG. 3 of the attached drawings;

(e) exhibiting an elemental analysis: C 32.5%, H 5.0%, N 5.8% and S 13.3%;

(f) giving a single spot at $R_f=0.59$ in a cellulose thin layer chromatography with acetonitrile-water (7:3) as the developing solvent and at $R_f=0.22$ in the same chromatography with propanol-water (8:2), and (g) losing its antibacterial activity when treated with hydroxylamine; and (h) exhibiting an activity inhibitory to $\beta$-lactamase; and the SF-2050B substance being further characterized by:

(a) being a dibasic acid which moves towards anode in a high-voltage filter paper electrophoresis at pH 6.4 and shows a mobility of 1.58 when the mobility of cephamycin A is assumed to be 1.0 in this electrophoresis;

and the di-sodium salt of SF-2050B substance being further characterized by:

(b) having characteristic absorption peaks at 228 nm and 305 nm in ultraviolet absorption spectrum in aqueous solution;

(c) having an infrared absorption spectrum pelleted in potassium bromide corresponding to that shown in FIG. 6 of the attached drawings (peaks at 3450, 1760, 1630, 1520, 1410, 1260, 1080, 940, 910 and 870 $cm^{-1}$);

(d) having a hydrogen nuclear magnetic resonance absorption spectrum in deutero-water corresponding to that shown in FIG. 7 of the attached drawings;

(e) having a circular dichroism spectrum corresponding to that shown in FIG. 8 of the attached drawings;

(f) exhibiting an elemental analysis: C 33.5%, H 3.9%, N 5.7% and S 13.8%;

(g) exhibiting a retention time of 22 minutes 20 seconds in a high-performance liquid chromatography in a column of 4 mm×30 cm of "μ Bondapak" (NH$_2$)(a product of Waters Co., U.S.A. and comprising a silica gel treated with aliphatic hydrocarbons) as developed with 0.3 ml per minute of 0.01 M buffered phosphate solution at pH 6.5;

(h) giving a single spot at $R_f=0.32$ in cellulose thin layer chromatography with 80% aqueous propanol (namely, a mixture of water and propanol at a ratio of 2:8 by volume) as the developing solvent and at $R_f=0.65$ in the same chromatography with acetonitrile-water (7:3), (i) losing its antibacterial activity when treated with hydroxylamine, and (j) exhibiting an activity inhibitory to $\beta$-lactamase.

The above-mentioned and further physico-chemical properties of the sodium salt of the SF-2050 substance of this invention which has been obtained as a purest sample in the form of amorphous powder by freeze-drying its neutal aqueous solution and possibly contains a few percent of water and an undectable trace of impurities are summarized below.

1. The sodium salt of SF-2050 substance is essentially in the form of di-sodium salt as the free acid is considered as a dibasic acid in view of the results of elemental analysis and electrophoresis.

2. The sodium salt of SF-2050 substance moves towards anode in a high-voltage filter paper electrophoresis in pyridine-buffered acetate solution at pH 6.7 and exhibits a mobility of 1.6 when assumed that cephamycin A exhibits a mobility of 1.0 in the same high-voltage filter paper electrophoresis.

3. The sodium salt is somewhat stable when it is stored in cold in the dried conditions. However, the sodium salt in aqueous solution is very instable under acidic conditions and instable under neutral conditions but shows a highest stability at a pH of 7–8. Even under neutral conditions, it can be decomposed rapidly at an elevated temperature. When a neutralized aqueous solution of the sodium salt is admixed with an equal volume of aqueous solution of 0.02 M hydroxylamine and subsequently the admixture is allowed to stand at ambient temperature for 30 minutes or more, the antibacterial activity disappears entirely and the characteristic absorption peak at 295 nm vanishes, too.

4. The sodium salt is readily soluble in water, less soluble in methanol and substantially insoluble in chloroform and ethyl acetate.

5. The SF-2050 substance (the sodium salt) shows no definite melting point and decomposes slowly at 150° C. or higher.

6. The sodium salt shows an elemental analysis: C 32.5%, H 5.0%, N 5.8% and S 13.3%.

Figure 1:
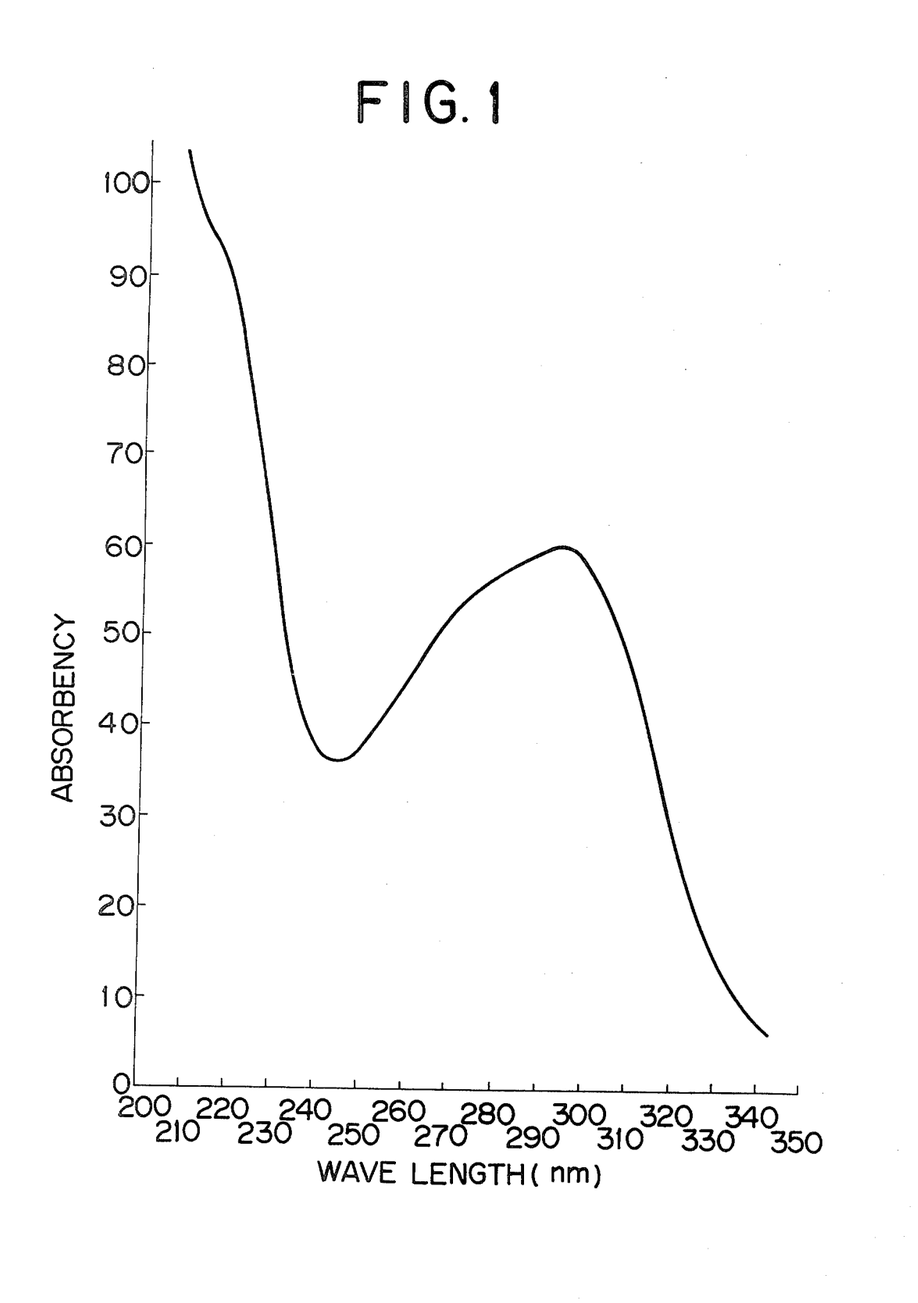
FIG. 1 shows a curve of the ultraviolet absorption spectrum of a sample of the sodium salt of SF-2050 substance of this invention (38 μg/ml in 1/200 M buffered phosphate solution at pH 7).

7. The sodium salt in a solution of 38 μg/ml of the sodium salt in M/200 buffered phosphate solution (pH 7) has a ultraviolet absorption spectrum shown in FIG. 1 of the attached drawings and exhibits a characteristic absorption peak at 295 nm.

8. The sodium salt pelleted in potassium bromide has an infrared absorption spectrum shown in FIG. 2 of the attached drawings.

9. The sodium salt in deutero-water has a hydrogen nucler magnetic resonance spectrum shown in FIG. 3 of the attached drawings.

10. Specific rotation $[\alpha]_D^{22} = -46°$ (c=0.1, $H_2O$).

Figure 4:
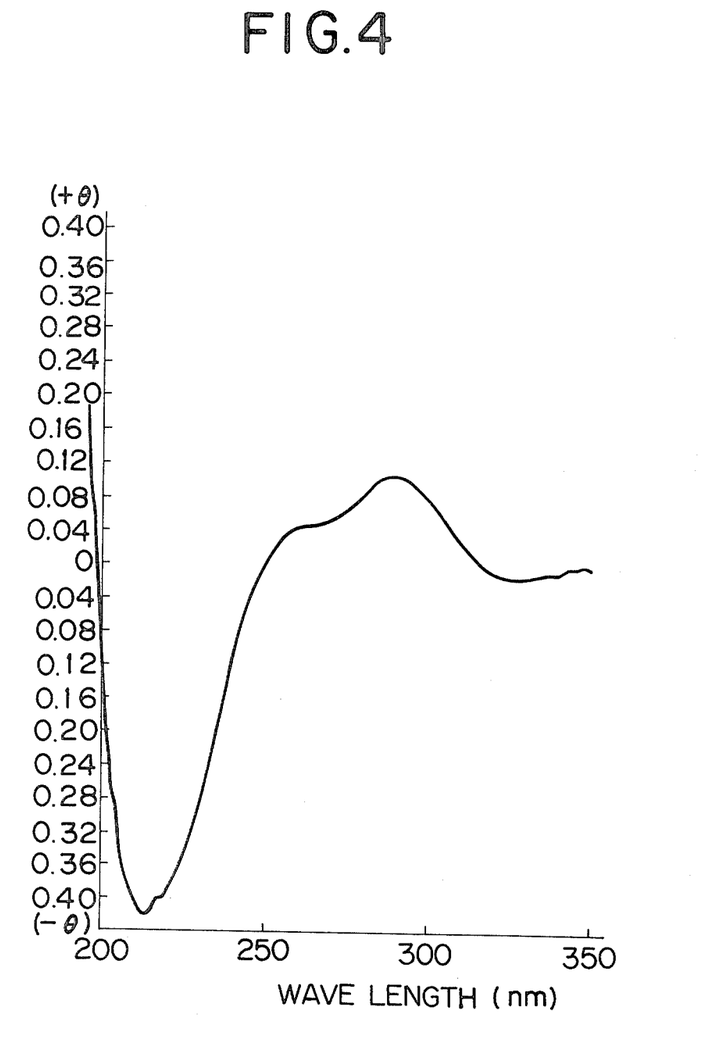
FIG. 4 shows a curve of the circular dichroism spectrum of a sample of the sodium salt of SF-2050 substance.

11. The sodium salt in water at the concentration of 1 mg/ml has a circular dichroism spectrum curve shown in FIG. 4 of the attached drawings.

12. The $R_f$ values in a cellulose thin layer chromatography are as follows:

(a) $R_f = 0.59$ when developed with acetonitrile-water (7:3), (c) $R_f = 0.22$ when developed with isopropanol-water (8:2).

13. The sodium salt is positive to the color reaction to indicate the presence of sufoxido group in the molecule. Thus, a sample of the sodium salt placed on a filter paper sheet or silica gel thin layer is treated with a spray of a mixture of 10 parts by volume of 0.5% aqueous sodium iodide and 1 part by volume of concentrated hydrochloric acid, followed by standing in dark for 15 minutes under reduced pressure in a desiccator containing dry solids of sodium hydroxide. The filter paper sheet or the thin layer is then removed from the desiccator and treated with a spray of an aqueous solution of 0.5% solublised starch, when purple colorisation takes place to indicate the liberation of elementary iodine.

The sodium salt is negative to the ninhydrin reaction.

Furthermore, the above-mentioned and further physico-chemical properties of the sodium salt of the SF-2050B substance which has been obtained as a purest sample in the form of amorphous powder by freeze-drying its neutral aqueous solution and possibly contains a few percent of water and an undectable trace of impurities are described below.

1. The sodium salt of SF-2050B substance is essentially in the form of di-sodium salt as the free acid is considered as a dibasic acid in view of the results of elemental analysis and electrophoresis.

2. The sodium salt of SF-2050B substance moves towards anode in a high-voltage filter paper electrophoresis in pyridine-buffered acetate solution at pH 6.4 and exhibit a mobility of 1.58 when assumed that cephamycin A exhibits a mobility of 1.0 in the same high-voltage filter paper electrophoresis.

3. The sodium salt is somewhat stable when it is stored as a solid powder in cold in the presence of a dehydrating agent. However, the sodium salt in aqueous solution is very instable under acidic conditions and instable under neutral conditions but shows a highest stability at a pH of 6.5–8. Even under neutral conditions it can be decomposed rapidly at an elevated temperature. When a neutralized aqueous solution of the sodium salt is admixed with an equal volume of an aqueous solution of 0.02 M hydroxylamine and subsequently the admixture is allowed to stand at ambient temperature for 30 minutes or more, the antibacterial activity disappears entirely and the characteristic absorption peak at 305 nm vanishes, too.

4. The sodium salt is readily soluble in water, less soluble in methanol and substantially insoluble in chloroform and ethyl acetate.

5. The SF-2050B substance (the sodium salt) shows no definite melting point and decomposes slowly at 150° C. or higher.

6. The sodium salt shows an elemental analysis: C 33.5%, H 3.9%, N 5.7% and S 13.8%.

Figure 5:
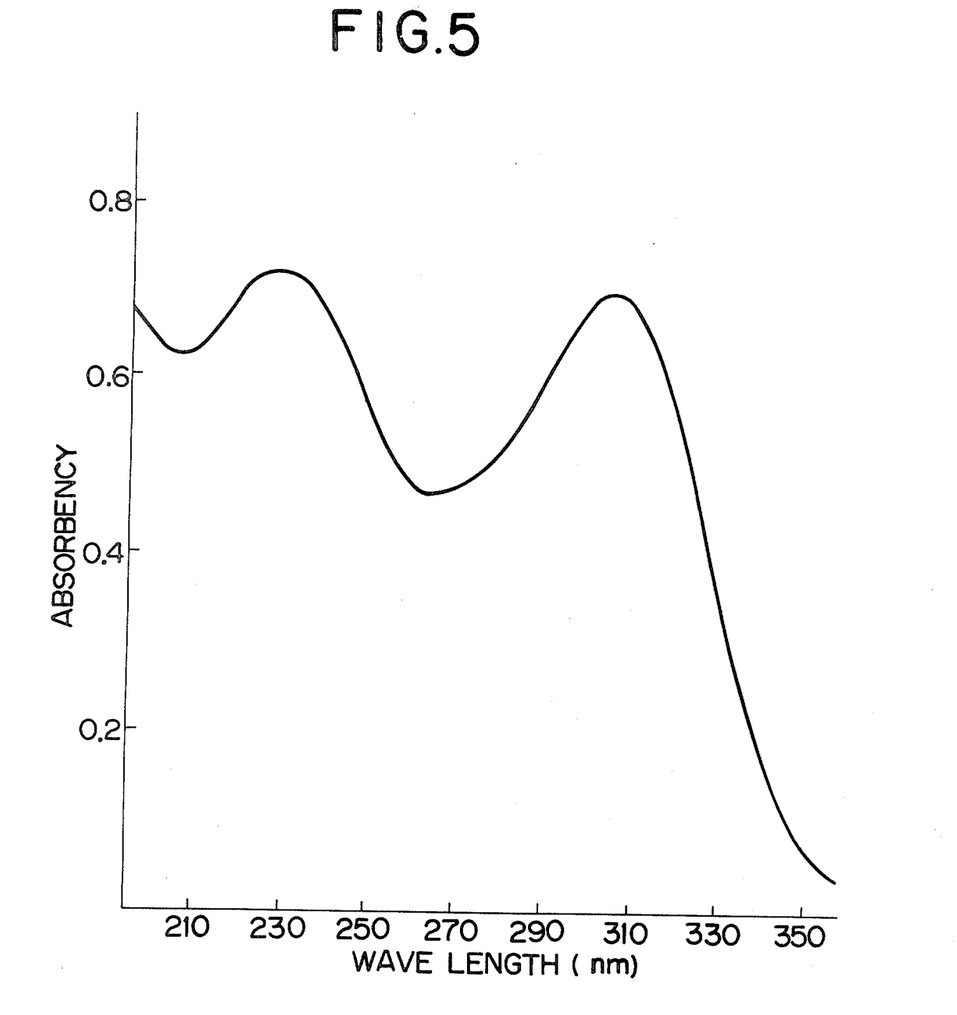
FIG. 5 shows a curve of the ultraviolet absorption spectrum of a sample of the sodium salt of SF-2050B substance of this invention (25 μg/ml, in 1/100 M buffered phosphate solution at pH 6.5).

7. The sodium salt in a solution of 25 μg/ml of the sodium salt in M/100 buffered phosphate solution (pH 6.5) has a ultraviolet absorption spectrum shown in FIG. 5 of the attached drawings and exhibits a characteristic absorption peak at 228 nm and 305 nm.

8. The sodium salt pelleted in potassium bromide has an infrared absorption spectrum shown in FIG. 6 of the attached drawings.

9. The sodium salt in deutero-water has a hydrogen nucler magnetic resonance spectrum shown in FIG. 7 of the attached drawings.

10. The sodium salt in 1/100 M buffered phosphate solution (pH 6.5) has a circular dichroism spectrum curve shown in FIG. 8 of the attached drawings.

11. The $R_f$ values in a cellulose thin layer chromatography are as follows:

(a) $R_f = 0.65$ when developed with acetonitrile-water (7:3), (b) $R_f = 0.32$ when developed with propanol-water (8:2).

12. In a high-performance liquid chromatography using "μ Bondapak" ($NH_2$) (a product of Waters Co., U.S.A.) (as a column of 4 mm × 30 cm), the sodium salt has a retention time of 22 minutes 20 seconds when developed with 1/100 M buffered phosphate solution (pH 6.5) at a flow rate of 0.3 ml/minute.

13. Color reaction:

Positive to potassium permanganate reaction and sodium iodide reaction, and negative to ninhydrin reaction.

Referring to the attached drawings.

The antibacterial activity of the SF-2050 substance and SF-2050B substance of this invention to inhibit the growth of various bacteria was estimated according to a conventional disc-plate method. Thus, the SF-2050 substance or SF-2050B substance (as the sodium salt) was dissolved in distilled water at concentrations indicated in Table 2 below. With the test solutions so prepared were impregnated paper-discs made of filter paper of 8 mm in diameter, which were subsequently air-dried. Each of these paper discs so treated was placed on a plate of an assaying incubation medium (1), (2) or (3) of the composition indicated in Table 2 below which was containing the test microorganism to be incubated therein and which was laid over the underlying layer of agar medium in the assaying dish. The incubation was made at a temperature of 37° C. for 16 hours. Subsequently the diameter of the inhibition zone formed around the paper disc was measured, and the test results so obtained are summarized in Table 2 below.

Table 2

| Test microorganism | Concentration of tested antibiotics (μg/ml) | Diameter of Inhibition zone (mm) SF-2050 substance | Diameter of Inhibition zone (mm) SF-2050B substance | Incubation medium |
|---|---|---|---|---|
| Bacillus stearothermophilus | 10 | 38.0 | 38.5 | (1) |
|  | 5 | 32.4 | 36.3 |  |
|  | 2.5 | 30.6 | 32.2 |  |
|  | 1.25 | 26.8 | — |  |
| Bacillus subtilis ATCC 6633 | 80 | 18.6 | 23.5 | (2) |
|  | 40 | 15.5 | 20.7 |  |
|  | 20 | 12.4 | 17.6 |  |
|  | 10 | 11.0 |  |  |
| Staphylococcus aureus 209P | 80 | 23.3 | 25.6 | (3) |
|  | 40 | 18.4 | 21.5 |  |
|  | 20 | 15.1 | 16.7 |  |
|  | 10 | 12.1 | — |  |
| Escherichia coli K-12 | 80 | 22.3 | 25.0 | (2) |
|  | 40 | 19.0 | 21.5 |  |
|  | 20 | 14.9 | 19.9 |  |
|  | 10 | 11.2 | — |  |
| Vibrio percolans | 10 | 21.9 | 22.5 | (2) |
|  | 5 | 18.7 | 19.0 |  |
|  | 2.5 | 14.8 | 16.4 |  |
|  | 1.25 | 12.0 | — |  |
| Proteus mirabiles | 80 | 24.5 | 30.0 | (2) |
|  | 40 | 21.0 | 28.2 |  |
|  | 20 | 17.9 | 23.6 |  |
|  | 10 | 14.6 | — |  |
| Klebsiella pneumoniae | 80 | 17.2 | 17.6 | (2) |
|  | 40 | 12.7 | 16.6 |  |
|  | 20 | 11.5 | 13.4 |  |
|  | 10 | — | — |  |

The incubation media (1), (2) and (3) shown in Table 2 above have the following compositions:

| Incubation medium (1) | | Incubation medium (2) | | Incubation medium (3) | |
|---|---|---|---|---|---|
| Glucose | 0.1% | Polypeptone | 0.5% | Polypeptone | 1.0% |
| Tryptone | 0.5% | Meat extract | 0.3% | Meat extract | 0.5% |
| Yeast extract | 0.25% | Agar | 1.5% | Sodium chloride | 0.25% |
| Agar | 1.5% |  |  | Agar | 1.5% |
| (pH 7.0) |  | (pH 7.0) |  | (pH 7.0) |  |

From the results of further tests, we have now found that the SF-2050 substance and SF-2050B substance both have an activity to inhibit the action of β-lactamase when determined by Sargent's method (M. G. Sargent, "Journal of Bacteriology" 95, 1493 (1968)). This is, according to Sargent's method, the activity inhibitory to β-lactamase is measured as follows:

Four reagents are prepared in the following ways:
  Reagent A: a penicillinase is dissolved in 0.1 M buffered phosphate solution (pH 7.0), and the resulting solution is diluted with the same buffered phosphate solution to a potency which exhibits a light absorbency (or optical density) of about 0.5 at light wave length of 490 nm when measured under the undermentioned conditions. Reagent B: A solution of 1.3% of penicillin G potassium salt in water. Reagent C: 0.1 M buffered phosphate solution, pH 7.0. Reagent D: Iodine-buffered acetate solution which has been prepared by the Sargent's method.

For the control test, 0.5 ml of reagent B and 2 ml of reagent C were placed together in a test tube and the mixture in the tube was subsequently heated at 30° C. for 5 minutes. Into this test tube was added 0.5 ml of reagent A, and the resulting admixture was kept at 30°

C. for 30 minutes for the reaction and further admixed with 5 ml of reagent D. After standing for 10 minutes, light absorbency (this may also be termed as optical density) of the reaction solution at light wave length of 490 nm was determined and expressed as value a. As the blank test for this control test, 0.5 ml of reagent B and 2 ml of reagent C were placed together in a test tube and the mixture in the tube was subsequently heated at 30° C. for 5 minutes. The content of the test tube was further kept at 30° C. for 30 minutes and admixed with 5 ml of reagent D and then immediately with 0.5 ml of reagent A. The admixture so obtained was allowed to stand for 10 minutes, and the absorbency of the resulting reaction solution at 490 nm was determined and expressed as value b. For the inhibition test of determining the inhibitory activity of SF-2050 or SF-2050B substance, 0.5 ml of reagent B and reagent C′ comprising a solution of SF-2050 or SF-2050B substance (as penicillinase-inhibitor) dissolved in reagent C to a proper inhibitor concentration were placed together in a test tube and the mixture was subsequently heated at 30° C. for 5 minutes. The content of the test tube was then reacted with 0.5 ml of reagent A and 5 ml of reagent D in the same way as in the aforesaid control test. The absorbency of the reaction solution at 490 nm was determined and expressed as value c. As the blank test for this inhibition test, the blank test for the aforesaid control test was repeated with using reagent C′ in place of reagent C. The absorbency of the reaction solution at 490 nm was also determined and expressed as value b′.

The above tests were made concurrently. Inhibition of the $\beta$-lactamase by the inhibitor was calculated according to the following equation:

$$\text{Inhibition (\%)} = (1 - \frac{b' - c}{b - a}) \times 100$$

As stated hereinbefore, the SF-2050 substance and SF-2050B substance are not only active againt gram-positive and gram-negative bacteria but also are active against resistant bacteria capable of producing $\beta$-lactamase, so that they are very useful antibiotic which are administrable as antibacterial agent for treatment of bacterial infections in human beings and stock animals. Furthermore, the SF-2050 substance and SF-2050B substance may be used as antibacterial agent or disinfectant for sterilisation of food products as well as surgical and therapeutic instruments. The SF-2050 substance and SF-2050B substance may be used either alone or in mixtures thereof, and they also may be used effectively in association with an $\beta$-lactam-type antibiotics, such as ampicillin.

The SF-2050 substance and SF-2050B substance of this invention, either in the form of the free acid or in the form of its pharmaceutically acceptable salt such as sodium salt and potassium salt, may be formulated into injectable solutions by dissolving at a suitable level into a physiological saline solution or other conventional pharmaceutically acceptable liquid carrier such as aqueous vehicles, for example, Ringer's injection, dextrose injection, or into another suitable administration forms by admixing with a pharmaceutically acceptable solid carrier such as talc, starch, calcium carbonate. For administration of the SF-2050 substance and SF-2050B substance, the injectable solutions prepared may be given intravenously, intramuscularly, or intraperitoneally. As an antibacterial agent, the SF-2050 substance and SF-2050B substance both may be administered at a dosage of 50 mg to 1500 mg and particularly 100 to 1000 mg for adult two, three or four times a day. Sutiable dosage may be about 2 mg to 500 mg/kg/day.

According to a further aspect of this invention, therefore, there is provided an antibacterial composition comprising as the active ingredient an antibacterially effective amount of at least one of the SF-2050 substance, SF-2050B substance and pharmaceutically acceptable salts thereof, in association with a pharmaceutically acceptable liquid or solid carrier for the active ingredient. The content of this active ingredient in this composition may be in a range of 5% to 50% by weight of the composition.

The invention is now illustrated with reference to the following Examples to which this invention is not limited in any way.

EXAMPLE 1 Production of the SF-2050 substance (1) Incubation of the strain SF-2050

A stock culture of Streptomyces sp. strain SF-2050 (identified as FERM-P 4358 or ATCC. 31450) was used, and a loopful amount of this stock culture was inoculated to 10 ml of a sterilized seed culture medium comprising 1.0% soluble starch and 3.0% soybean meal (pH 7.0 before the sterilization) which was placed in a thick test tube of 50 ml capacity. The incubation was made at 28° C. for 48 hours. One ml portion of the seed culture so obtained were inoculated to five Sakaguchi flasks of 500 ml capacity each containing 100 ml of the seed culture medium, and the flasks were incubated at 28° C. for 24 hours. The second seed culture so obtained (500 ml) was further inoculated to 20 l of the seed culture medium of the same composition as above in a 30 liters jar-fermentor. The inoculated medium was incubated at 28° C. for 24 hours under aeration and agitation. The third seed culture so obtained (15 liters) was then inoculated to 200 l of a production culture medium in a 300 liters jar-fermentor. This production culture medium employed comprised 2.0% glucose, 1.0% soybean meal, 0.1% $K_2HPO_4$, 0.02% $CaCO_3$, and 0.0001% $CoCl_2.6H_2O$ (pH 6.5 before the sterilization). The incubation was made at 28° C. for 44 hours under aeration and agitation. After the incubation, the culture broth was filtered with aid of diatomaceous earth to give 170 liters of the broth filtrate.

(2) Recovery of the SF-2050 substance

The borth filtrate so obtained (170 liters) was passed through a column of 10 l of active carbon for the adsorption of the active substances. The carbon column was washed twice with 6 l portions of water and then eluted with 50% aqueous acetone. The eluate was collected in 8-liters fractions, and four fractions Nos. 1, 2, 3 and 4 were taken. The fraction Nos. 2 and 3 were combined together and concentrated to a volume of 7 liters by distilling off the acetone under reduced pressure. The resulting concentrated solution was admixed with 7 liters of dichloromethane containing 0.2% (w/v) of benzyldimethylcetyl ammonium chloride under agitation for the extraction of the active substances. The dichloromethane layer was again extracted with 700 ml of water containing 1% (w/v) of sodium iodide for transfer of the active substances into the water phase. The resulting aqueous extract was passed through a column of 1 liter of DEAE-Sephadex A-25 (a gel-filtration agent, a product of Pharmacia Co., Sweden) which had been buffered by treating with a buffered phosphate solution (pH 7). In this way, the active substances were absorbed by said DEAE-Sephadex A-25 column, which was subsequently washed with 6 liters of a solution containing 0.1 M sodium chloride dissolved in 20 mM buffered phosphate solution (pH 7). The elution of the active substances from said column was then conducted using as the eluent a solution containing 0.14 M sodium chloride dissolved in further volume of the same buffered phosphate solution (pH 7). The eluate was collected in 150 ml-fractions to afford the active fraction Nos. 32–52 containing the SF-2050 substance sodium salt, as well as the active fractions Nos. 78–98 containing the SF-2050B substance sodium salt.

The fractions Nos. 32–52 were combined together and passed through a column of 25 ml of active carbon for the adsorption of the active substance (the SF-2050 substance sodium salt). This active carbon column was washed twice with 10 ml portions of water and then eluted with 290 ml of 50% aqueous acetone for the isolation of the active substance. The eluate was concentrated to 110 ml by evaporation of water and acetone under reduced pressure, and the resulting concentrate was passed through a column of 100 ml of DEAE-Sephadex A-25 which had been buffered by treating with a buffered phosphate solution (pH 7), to make the adsorption of the active substance. This column was then eluated using as the development solvent a solution containing 50 mM sodium chloride dissolved in 20 mM buffered phosphate solution (pH 7). The eluate was collected in 100 ml-fractions, and the active fractions Nos. 30–37 were combined together and passed through a column of 8 ml of active carbon for the adsorption of the active substance. This active carbon column was washed twice with 3 ml portions of water and then eluted with 150 ml of 50% aqueous acetone to isolate the SF-2050 substance sodium salt. The eluate so obtained was concentrated to 7 ml under reduced pressure, and the resulting concentrated solution was freeze-dried to give a colorless powder of the sodium salt of the SF-2050 substance. Yield 10.4 mg. $[\alpha]_D^{22} = -46°$ (c=0.1, $H_2O$).

EXAMPLE 2 Production of the SF-2050B substance (1) Incubation of the strain SF-2050

A stock culture of Streptomyces sp. strain SF-2050 (identified as FERM-P 4358 or ATCC. 31450) was used, and a loopful amount of this stock culture was inoculated to 10 ml of a sterilized seed culture medium comprising 1.0% soluble starch and 3.0% soybean meal (pH 7.0 before the sterilization) which was placed in a thick test tube of 50 ml capacity. The incubation was made at 28° C. for 48 hours. One ml portions of the seed culture so obtained was inoculated to five Sakaguchi flasks of 500 ml capacity each containing 100 ml of the seed culture medium, and the flasks were incubated at 28° C. for 24 hours. The second seed culture so obtained (500 ml) was further inoculated to 20 l of the seed culture medium of the same composition as above in a 30 liters jar-fermentor. The inoculated medium was incubated at 28° C. for 24 hours under aeration and agitation. The third seed culture so obtained (15 liters) was then inoculated to 200 l of a production culture medium in a 300 liters jar-fermentor. This production culture medium employed comprised 2.0% glucose, 1.0% soybean meal, 0.1% $K_2HPO_4$, 0.02% $CaCO_3$ and 0.0001% $CoCl_2.6H_2O$ (pH 6.5 before the sterilization). The incubation was made at 28° C. for 44 hours under aeration and agitation. After the incubation, the culture broth was filtered with aid of diatomaceous earth to give 170 liters of the broth filtrate.

(2) Recovery of the SF-2050B substance

The broth filtrate so obtained (170 liters) was passed through a column of 10 l of active carbon for the adsorption of the active substances. The carbon column was washed twice with 12 l portions of water and then eluted with 50% aqueous acetone. The eluate was collected in 8-liters fractions, and four fractions Nos. 1, 2, 3 and 4 were taken. The fraction Nos. 2 and 3 are combined together and concentrated to a volume of 7 liters by distilling off the acetone at 38° C. under reduced pressure. The resulting concentrated solution was admixed with 7 liters of dichloromethane containing 0.2% (w/v) of benzyldimethylcetyl ammonium chloride under agitation for the extraction of the active substances. The dichloromethane layer was again extracted with 700 ml of water containing 1% (w/v) of sodium iodide for transfer of the active substances into the water phase. The resulting aqueous extract was concentrated by distilling off the dichloromethane under reduced pressure. The concentrated aqueous extract so obtained was then passed through a column of 1 liter of DEAE-Sephadex A-25 (a gel-filtration agent, a product of Pharmacia Co., Sweden) which had been buffered by treating with a buffered phosphate solution (pH 7.2). In this way, the active substances were absorbed by said DEAE-Sephadex A-25 column, which was subsequently washed with 3 liters of a 20 mM buffered phosphate solution (pH 7.2) and then with 6 liters of a solution containing 0.1 M sodiun chloride dissolved in 20 mM buffered phosphate solution (pH 7.2). The elution of the active substances from said column was then conducted using as the eluent a solution containing 0.14 M sodium chloride dissolved in a further volume of the same buffered phosphate solution (pH 7.2). The active substances were eluted from the DEAE-Sephadex A-25 column during the period of time when there had been passed through the column a volume of the eluent which amounted to about 12 to 14 times as much as the volume of the column. Thus, the eluate was collected in 150 ml-fractions to afford the active fraction containing the SF-2050 substance sodium salt, as well as the active fractions Nos. 78–98 (about 2.1 liters in total) containing the SF-2050B substance sodium salt.

The active fractions Nos. 78–98 were combined together and passed through a column of 30 ml of active carbon for the adsorption of the active substance (the SF-2050B substance sodium salt). This active carbon column was washed twice with 50 ml portions of water and then eluted with 120 ml of 50% aqueous acetone for the isolation of the active substance. The eluate was concentrated by evaporation of water and acetone under reduced pressure, and the resulting concentrated solution was freeze-dried to give 62 mg of a colorless, crude powder of the sodium salt of the SF-2050B substance.

(3) Purification of the SF-2050B substance

The crude powder of the SF-2050B substance obtained as above (62 mg) was taken up into 2 ml of 20 mM buffered phosphate solution (pH 7.2), and the resultant solution was passed through a column of 120 ml of DEAE-Sephadex A-25 which had been buffered by treating with the buffered phosphate solution (pH 7.2), so that the active substance was adsorbed by the column. This column was subsequently washed with 600 ml of 20 mM buffered phosphate solution (pH 7.2) and then eluted using as the eluent a solution containing 0.1 M sodium chloride dissolved in a further volume of the same 20 mM buffered phosphate solution (pH 7.2). The active substance (that is, the SF-2050B substance sodium salt) was eluted out of the column during the period of time where there had been passed through the column a volume of the eluent which amounted to 18 to 22 times as much as the volume of the column. During this elution procedure, the eluate was collected in 18 ml-fractions, and the active fractions Nos. 118–146 (about 480 ml in total) containing the SF-2050B substance sodium salt were afforded. These active fractions combined were passed through a column of 10 ml of active carbon for the adsorption of the active substance.

This active carbon column was washed with 40 ml of water and then eluted with 50 ml of 50% aqueous acetone. The eluate was concentrated to a volume of about 3 ml by distilling off the acetone under reduced pressure, and the concentrated solution was freeze-dried to give a pure, colorless powder of the SF-2050B substance sodium salt. Yield 2.2 mg.

What we claim is:

1. A process for the production of SF-2050 substance and/or SF-2050B substance, which comprises:

cultivating a strain of the genus Streptomyces capable of producing SF-2050 substance and SF-2050B substance in an aqueous liquid culture medium containing assimilable carbon and nitrogen sources under aerobic conditions for a period of time sufficient to produce and accumulate at least one of SF-2050 substance and SF-2050B substance in the culture, and then recovering at least one of the SF-2050 substance and SF-2050B substance from the culture.

2. A process according to claim 1 in which Streptomyces sp. SF-2050 identified as FERM-P 4358 or as ATCC. 31450 is cultivated under aerobic conditions.

3. A process according to claim 1 in which the SF-2050 substance is recovered from the culture broth of Streptomyces sp. SF-2050.

4. A process according to claim 1 in which the SF-2050B substance is recovered from the culture broth of Streptomyces sp. SF-2050.

5. A substance selected from the SF-2050 substance, SF-2050B substance and pharmaceutically acceptable salts thereof; the SF-2050 substance and SF-2050B substance being both a dibasic acid compound of which the sodium salt is in the form of a colorless powder having no definite melting point and shows negative reaction with ninhydrin but positive reaction with sodium iodide and of which the di-sodium salt is a colorless powder soluble in water, less soluble in methanol and sparingly soluble in ethyl acetate, chloroform and benzene;

the SF-2050 substance being further characterized by:

(a) being a dibasic acid which moves towards anode in a high-voltage filter paper electrophoresis at pH 6.7 and shows a mobility of 1.6 when the mobility of cephamycin A is assumed to be 1.0 in this electrophoresis;

and the di-sodium salt of the SF-2050 substance being further characterized by:

(b) having a characteristic absorption peak at 295 nm in ultraviolet absorption sepectrum in aqueous solution;

(c) having an infrared absorption spectrum pelleted in potassium bromide corresponding to that shown in FIG. 2 of the attached drawings;

(d) having a hydrogen nuclear magnetic resonance absorption spectrum in deutero-water corresponding to that shown in FIG. 3 of the attached drawings:

(e) exhibiting an elemental analysis: C 32.5%, H 5.0%, N 5.8% and S 13.3%;

(f) giving a single spot at $R_f=0.59$ in a cellulose thin layer chromatography with acetonitrile-water (7:3) and at $R_f=0.22$ in the same chromatography with propanol-water (8:2), and (g) losing its antibacterial activity when treated with hydroxylamine; and (h) exhibiting an activity inhibitory to $\beta$-lactamase;

and the SF-2050B substance being further characterized by:

(a) being a dibasic acid which moves towards anode in a high-voltage filter paper electrophoresis at pH 6.4 and shows a mobility of 1.58 when the mobility of cephamycin A is assumed to be 1.0 in this electrophoresis;

and the di-sodium salt of SF-2050B substance being further characterized by:

(b) having characteristic absorption peaks at 228 nm and 305 nm in ultraviolet absorption spectrum in aqueous solution;

(c) having an infrared absorption spectrum pelleted in potassium bromide corresponding to that shown in FIG. 6 of the attached drawings;

(d) having a hydrogen nuclear magnetic resonance absorption spectrum in deutero-water corresponding to that shown in FIG. 7 of the attached drawings;

(e) having a circular dichroism spectrum corresponding to that shown in FIG. 8 of the attached drawings;

(f) exhibiting an elemental analysis: C 33.5%, H 3.9%, N 5.7% and S 13.8%;

(g) exhibiting a retention time of 22 minutes 20 seconds in a high-performance liquid chromatography in a column of 4 mm×30 cm of "$\mu$Bondapak" (NH$_2$) (a product of Waters Co., U.S.A.) as developed with 0.3 ml per minute of 0.01 M buffered phosphate solution at pH 6.5;

(h) giving a single spot at $R_f=0.32$ in a cellulose thin layer chromatography with 80% aqueous propanol (namely, a mixture of water and propanol at a ratio of 2:8 by volume) and at $R_f=0.65$ in the same chromatography with acetonitrile-water (7:3), (i) losing its antibacterial activity when treated with hydroxylamine, and (j) exhibiting an activity inhibitory to $\beta$-lactamase.

6. The substance according to claim 5 which is the SF-2050 substance or the SF-2050 substance sodium salt.

7. The substance according to claim 5 which is the SF-2050B substance or the SF-2050B substance sodium salt.

8. An antibacterial composition comprising as the active ingredient an antibacterially effective amount of at least one of the SF-2050 substance, SF-2050B substance as defined in claim 5 and pharmaceutically acceptable salts thereof, in association with a pharmaceutically acceptable carrier for the active ingredient.

* * * * *